United States Patent
Liu et al.

(10) Patent No.: US 11,234,629 B2
(45) Date of Patent: Feb. 1, 2022

(54) METHOD AND DEVICE FOR SELF-LEARNING DYNAMIC ELECTROCARDIOGRAPHY ANALYSIS EMPLOYING ARTIFICIAL INTELLIGENCE

(71) Applicant: Shanghai Lepu CloudMed Co., Ltd, Shanghai (CN)

(72) Inventors: Chang Liu, Beijing (CN); Chuanyan Hu, Beijing (CN); Weiwei Zhou, Beijing (CN); Haitao Lu, Beijing (CN); Jiayu Wang, Beijing (CN); Jun Cao, Beijing (CN)

(73) Assignee: Shanghai Lepu CloudMed Co., LTD., Shanghai (CN)

( * ) Notice: Subject to any disclaimer, the term of this patent is extended or adjusted under 35 U.S.C. 154(b) by 70 days.

(21) Appl. No.: 16/651,912

(22) PCT Filed: Jan. 12, 2018

(86) PCT No.: PCT/CN2018/072359
§ 371 (c)(1),
(2) Date: Mar. 27, 2020

(87) PCT Pub. No.: WO2019/100565
PCT Pub. Date: May 31, 2019

(65) Prior Publication Data
US 2020/0260980 A1   Aug. 20, 2020

(30) Foreign Application Priority Data
Nov. 27, 2017  (CN) .......................... 201711203048.2

(51) Int. Cl.
*A61B 5/316*     (2021.01)
*A61B 5/00*      (2006.01)
(Continued)

(52) U.S. Cl.
CPC .............. *A61B 5/316* (2021.01); *A61B 5/352* (2021.01); *A61B 5/364* (2021.01); *A61B 5/366* (2021.01);
(Continued)

(58) Field of Classification Search
None
See application file for complete search history.

(56) References Cited

U.S. PATENT DOCUMENTS

| | | | |
|---|---|---|---|
| 6,370,423 | B1 | 4/2002 | Guerrero et al. |
| 2014/0005988 | A1 | 1/2014 | Brockway |
| 2014/0249437 | A1 | 9/2014 | Zong et al. |

FOREIGN PATENT DOCUMENTS

| | | |
|---|---|---|
| CN | 102138789 B | 5/2014 |
| CN | 107358196 A | 11/2017 |

(Continued)

OTHER PUBLICATIONS

European Search Report and Search Opinion Received for EP Application No. 18881678, dated Jun. 11, 2021, 10 pages.

(Continued)

*Primary Examiner* — Ankit D Tejani
(74) *Attorney, Agent, or Firm* — TraskBritt

(57) ABSTRACT

A self-learning dynamic electrocardiography analysis method employing artificial intelligence. The method comprises: pre-processing data, performing cardiac activity feature detection, interference signal detection and cardiac activity classification on the basis of a deep learning method, performing signal quality evaluation and lead combination, examining cardiac activity, performing analytic computations on an electrocardiogram event and parameters, and then automatically outputting report data. The method achieves an automatic analysis method for a quick and comprehensive dynamic electrocardiography process, and (Continued)

recording of modification information of an automatic analysis result, while also collecting and feeding back modification data to a deep learning model for continuous training, thereby continuously improving and enhancing the accuracy of the automatic analysis method. Also disclosed is a self-learning dynamic electrocardiography analysis device employing artificial intelligence.

19 Claims, 6 Drawing Sheets

(51) Int. Cl.
    *A61B 5/352*     (2021.01)
    *A61B 5/364*     (2021.01)
    *A61B 5/366*     (2021.01)
(52) U.S. Cl.
    CPC .......... *A61B 5/7203* (2013.01); *A61B 5/7267* (2013.01); *A61B 5/7271* (2013.01)

(56) References Cited

FOREIGN PATENT DOCUMENTS

| CN | 106108889 B | 11/2019 |
|---|---|---|
| EP | 2033574 A1 | 3/2009 |
| WO | 2017/072250 A1 | 5/2017 |

OTHER PUBLICATIONS

Vollmer Marcus et al: "Can supervised learning be used to classify cardiac rhythms?", 2017 Computing in Cardiology (CINC), CCAL, Sep. 24, 2017 (Sep. 24, 2017), pp. 1-4.

Chinese Office Action for Chinese Application No. 201711203048.2 dated Mar. 18, 2019, 10 pages.

International Search Report for International Application No. PCT/CN2018/072359 dated May 30, 2018, 2 pages.

International Written Opinion for International Application No. PCT/CN2018/072359 dated May 30, 2018, 3 pages.

METHOD AND DEVICE FOR SELF-LEARNING DYNAMIC ELECTROCARDIOGRAPHY ANALYSIS EMPLOYING ARTIFICIAL INTELLIGENCE

CROSS-REFERENCE TO RELATED APPLICATIONS

This application is a national phase entry under 35 U.S.C. § 371 of International Patent Application PCT/CN2018/072359, filed Jan. 12, 2018, designating the United States of America and published as International Patent Publication WO 2019/100565 A1 on May 31, 2019, which claims the benefit under Article 8 of the Patent Cooperation Treaty to Chinese Patent Application Serial No. 201711203048.2, filed Nov. 27, 2017.

TECHNICAL FIELD

The present disclosure relates to the technical field of artificial intelligence data analysis, and more particularly, to an artificial intelligence self-learning-based ambulatory electrocardiogram analysis method and apparatus.

BACKGROUND

Non-invasive electrocardiogram examination is an important tool for analysis and screening of cardiovascular diseases (CVD). In non-invasive electrocardiogram examination, ambulatory electrocardiogram (Dynamic Electrocardiography, DCG) technology was first applied by Holter in 1957 for the research of monitoring cardiac electrophysiological activities, so it is also called Holter electrocardiograph, which has become one of important analysis methods of non-invasive examination in clinical cardiovascular field. The ambulatory ECG may continuously record a whole process of ECG activities for more than 24 hours, including ECG information under different conditions such as rest, activities, meals, work, study and sleep. The ambulatory ECG may find non-sustained arrhythmias that are not easily found by routine ECG examination, and especially may improve a detection rate of transient arrhythmia and transient myocardial ischemic attack, which is an important objective basis for clinical analysis of diseases, establishment of analysis and judgment of curative effect. In addition, the ambulatory ECG may determine whether symptoms such as palpitation, dizziness, fainting of patients are related to arrhythmia, such as sinus bradycardia, conduction block, rapid atrial fibrillation, paroxysmal supraventricular tachycardia, sustained ventricular tachycardia, which is one of the most important and most widely used situations of 24-hour ambulatory ECG at present.

Compared with ordinary ECG, the ambulatory ECG expands the scope of clinical application of ECG, and has a wide range of applications in hospitals, families, physical examination centers and communities.

The ambulatory ECG analysis device mainly includes three parts: ECG signal acquisition recorder, lead system and computer analysis software. The signal acquisition recorder is responsible for recording and storing ECG data of patients for 24 hours or even many days. Since the patient's body gesture changes frequently in daily activities, and is interfered by many situations, requirements for frequency response, sample frequency, resolution, impedance, and anti-interference performance of signal acquisition are relatively high. Waveforms of ECG signals collected by a high-performance ECG recorder have a high signal-to-noise ratio and high signal fidelity, which is very helpful for subsequent analysis and calculation. The lead system includes electrode plates and lead wires. The analysis and calculation software perform arrhythmia analysis, long intermittent arrest, flutter and fibrillation, conduction block, premature beat and escape beat, bradycardia, tachycardia, ST segment change detection, and analysis and classification of ECG events on collected digital signals, and helps doctors to analyze and report.

Different from a standard 12-lead system used in clinical resting ECG, Holter generally uses Mason-Likar lead system. In order to further improve the adaptability of the ambulatory ECG, medical experts have invented a reduced Mason-Likar (M-L) lead system. Common reduced M-L lead system measures data of four leads I, II, V2 and V5, or, I, II, V1 and V5, and it may calculate data of four leads III, aVR, aVL and aVF according to a relationship of ECG vectors, and analyze and show data of three leads II, V5 and aVF. The reduced M-L lead system Holter is a mainstream product in the market. However, since lead data from the reduced M-L lead system Holter cannot accurately analyze ST segment changes, some medical institutions also require to use 12-lead Holter for examination. With popularized applications of mobile health and wearable devices, now single-lead heart patches with a real-time monitoring function have also become popular in some specific populations, such as patients after percutaneous coronary intervention (PCI), pacemaker users, and long-distance runners.

The analysis of the ambulatory ECG includes the following steps: firstly, signal filtering processing is performed, and then the most significant P-QRS-T complex features in heart beats are detected and identified. Secondly, for characteristic signals such as identified QRS complex, P wave, T wave, R-R interval, P-R interval, ST segment and so on, the heart beats are classified according to the cardiac electrophysiological activities. And finally, considering the classification of the heart beats and rhythmic characteristics of the heart beats, some regular continuous activities of the heart beats are further summarized as heart rhythm events. ECG specialists analyze and describe the ambulatory ECG examination of patients according to the classification of the heart beats and the heart rhythm events.

Since signals generated by the electrophysiological activities of heart cells are weak (millivolt level), normal ECG signals have a frequency range of 0.01 Hz-100 Hz, in which 90% of the energy is concentrated in a range of 0.25 Hz-35 Hz. Therefore, during a 24-hour long-term continuous wearing process, the signals of the ambulatory ECG, are easily interfered. Main interferences include power line interference, which is an interference including 50 Hz and its harmonics generated by human capacitances, equipment circuits, leads and the like), electromyography interference, which is usually an irregular 5-2000 Hz high-frequency interference caused by muscle activities), baseline drift, which is caused by poor electrode contact, skin impedance, respiratory movement, etc., and the frequency range of which is generally between 0.05 Hz and 2.00 Hz very close to frequency components of the ST segment and Q wave of the ECG signals).

Traditional digital signal analysis of the ambulatory ECG is based on a paper (1) published by Pan and Tompkins in 1985. This method designs a signal analysis and calculation process: signal filtering; signal amplification; signal difference; according to some routine rules of the ECG signals and the cardiac electrophysiological activities, features of each P-QRS-T complex are found through the calculation of some adaptive thresholds; according to each found P-QRS-T complex and complexes before and after, each heart beat is classified and identified; based on the classification and recognition of the heart beats, various events such as arrhythmia and conduction block are generated through analyzing change rules of the heart beats; and doctors carefully review the heart beats and events by using some client analysis tools, and finally give an analysis description. At the same time, a typical 8-second segment of each event is captured from 24-hour ambulatory ECG data to generate an analysis report. Test results refer to an arrhythmia standard database from Massachusetts Institute of Technology (MIT) show that the recognition accuracy rate of this method reaches 99.3%, which becomes a classical analysis method in machine recognition methods for the ambulatory ECG. The analysis methods for such mainstream ambulatory ECG devices in the market are basically developed based on the content of Pan-Tompkins paper.

However, there are main problems of the above methods as follows: Firstly, the anti-interference ability is relatively poor due to the influence of interference signals. The classification and recognition of the heart beats cannot actively exclude the influence of interference fragments. Secondly, P and T cannot be accurately identified in feature extraction for the heart beats. There are often excessive detection and missed detection in heart beat detection. For some special ECG signals, such as tall T waves of patients with slow heart rhythm or signals of T wave hypertrophy, the excessive detection is often easy to occur. Thirdly, the classification of the heart beats basically stays in three types of sinus, supraventricular and ventricular, which is far from meeting complicated and comprehensive analysis requirements of ECG doctors. Fourthly, atrial flutter and atrial fibrillation, pacemaker heart beats and ST-T changes cannot be accurately identified. Therefore, it cannot help patients with atrial flutter and atrial fibrillation, there is of little significance in helping to evaluate the function of the pacemaker, and it cannot accurately analyze the help of the ST-T changes on myocardial ischemia. Fifthly, the identification of the heart beats and ECG events is not accurate and comprehensive, the heart beats and ECG events are easily missed due to the influence of many previous factors and it will also affect the interpretation of doctors. Sixthly, analysis methods in the prior art do not objectively evaluate the signal quality of event segments, and do not perform comprehensive analysis and statistics on the 24-hour data. Report summaries and event screenshots still rely on experiences and abilities of doctors, which easily results in an error that the data do not reflect the overall detection, missing report events, and poor or atypical screenshots of patient reports. Seventhly, due to the problems mentioned above, it is impossible to achieve automatic analysis to the final automatic report. Doctors still need to spend a lot of precious time carefully reading the ambulatory ECG data, which cannot fundamentally help doctors to improve their analysis ability, both in quality and efficiency.

At present, although many manufacturers have modified core methods in different degrees, which improves the overall recognition accuracy, due to the complex variability of the ambulatory ECG signals themselves of patients, especially the existence of various extreme interferences mentioned above, it is difficult to obtain test results of the standard database from MIT using the Pan-Tompkins method and subsequent improvements by various manufacturers in the application process. In practice, the recognition accuracy is less than 60%. Many researchers are also trying to use other methods to improve extraction and recognition of the P-QRS-T complex features, among which the wavelet transform method published by Cuiwei Li et al., in 1995 is relatively influential.

There is no classical method similar to Pan-Tompkins for the classification of heart rhythm events. The common method is to perform more complex signal morphological analysis based on QRS detection, and to summarize the heart beat events according to some basic principles of the ambulatory ECG. As mentioned above, the inevitable existence of a large number of interferences, the difference in the quality of signal acquisition of each lead, and individual differences of patients themselves make these methods difficult to achieve satisfactory results. In recent years, there have been new methods that try to improve the classification accuracy, such as mathematically complex wavelet transform methods and Hilbert-Huang transform methods. However, judging from the actual usage, there is still not great breakthrough. The main problem is still that the recognition accuracy is relatively low, and the classification of the heart events that may be recognized is not sufficient to cover needs of the examination and analysis for the ambulatory ECG.

Although most of the ambulatory ECG analysis software in the market may automatically analyze the data, due to the complexity and variability of the ambulatory ECG signals themselves, it is easy to be subjected to various interferences during the wearing process. In addition, for an average of about 100,000 heart beats in a 24-hour period, the accuracy rate of current automatic analysis software is far from enough to help doctors correctly analyze ECG data and give correct analysis reports in a relatively short time.

Therefore, how to help hospitals, especially a vast number of basic hospitals at all levels, effectively improve an automatic analysis level of the ambulatory ECG by using the most advanced scientific and technological method, artificial intelligence technology, under a difficult condition that there are not enough professional doctors to interpret the ambulatory ECG, is a difficult problem and challenge to be solved by the present disclosure.

BRIEF SUMMARY

The purpose of the present disclosure is to provide an artificial intelligence self-learning-based ambulatory electrocardiogram analysis method and apparatus, which may automatically, quickly and completely analyze measurement data output by an ECG device, and obtain required report data.

To achieve the above purpose, a first aspect of embodiments of the present disclosure provides the artificial intelligence self-learning-based ambulatory electrocardiogram analysis method, including:

receiving ambulatory electrocardiogram data output by an ambulatory electrocardiogram monitoring device; and converting a data format of the ambulatory ECG data into a preset standard data format by resampling, and performing a first filtering processing on converted ambulatory ECG data in the preset standard data format;

performing heart beat detection processing on ambulatory ECG data processed by the first filtering processing to identify multiple pieces of heart beat data comprised in the ambulatory ECG data, wherein each piece of heart beat data corresponds to a heart beat cycle, comprising amplitude and starting-ending time data of corresponding P wave, QRS complex and T wave;

determining a detection confidence level of each heart beat according to the heart beat data;

performing interference identification on the heart beat data according to a trained interference identification two-classification model to obtain whether there is interference noise in the heart beat data with a probability value for judging the interference noise;

determining a validity of the heart beat data according to the detection confidence level, and, according to lead parameters of determined valid heart beat data and the determined valid heart beat data, combining and generating heart beat time sequence data based on results of the interference identification and time rules; and generating heart beat analysis data according to the heart beat time sequence data;

performing feature extraction and analysis of an amplitude and time characterization data on the heart beat analysis data according to a trained heart beat classification model, to obtain primary classification information of the heart beat analysis data;

inputting the heart beat analysis data of particular heart beats in results of the primary classification information into a trained ST segment and T wave change model for identification, and determining ST segment and T wave evaluation information;

performing P wave and T wave feature detection on the heart beat analysis data according to the heart beat time sequence data to determine detailed feature information of P wave and T wave in each heart beat, wherein the detailed feature information comprises data of amplitudes, directions, forms and starting-ending time;

performing secondary classification processing on the heart beat analysis data according to ECG basic rule reference data, the detailed feature information of the P wave and the T wave and the ST segment and T wave evaluation information, under the primary classification information to finally obtain heart beat classification information;

analyzing and evaluating a signal quality of the heart beat analysis data, and obtaining a signal quality evaluation index of the heart beat analysis data;

analyzing and matching the heart beat classification information according to the ECG basic rule reference data, and processing a result of the analyzing and matching according to the signal quality evaluation index to generate ECG event data; and statistically analyzing the ECG event data to obtain corresponding report conclusion data and report table item data; evaluating the ECG event data according to the signal quality evaluation index to generate report graphic data; and outputting the report table item data, the report graphic data and the report conclusion data.

Preferably, the determining a detection confidence level includes:

determining an RR interval according to the heart beat data and calculating an estimation value of noise in the RR interval; and determining the detection confidence level of each piece of heart beat data according to the estimation value of the noise and a maximum amplitude in each piece of heart beat data.

Preferably, the performing interference identification on the heart beat data according to a trained interference identification two-classification model includes:

performing cutting and sampling on the heart beat data with a first data amount, and inputting data obtained by the cutting and sampling into the interference identification two-classification model to identify interference;

identifying a data segment with a heart beat interval greater than or equal to a preset interval determination threshold in the heart beat data;

performing a judgment of signal abnormality on the data segment with the heart beat interval greater than or equal to the preset interval determination threshold to determine whether the data segment is an abnormal signal;

if the data segment is not an abnormal signal, according to a set time value, determining a starting data point and an ending data point of sliding sampling in the data segment with a preset time width, and performing the sliding sampling on the data segment from the starting data point until the ending data point to obtain multiple sample data segments; and performing the interference identification on each of the multiple sample data segments.

Preferably, the generating heart beat analysis data according to the heart beat time sequence data includes:

cutting the heart beat data of each lead in the heart beat time sequence data according to a preset threshold to generate the heart beat analysis data of each lead.

Preferably, the performing feature extraction and analysis of an amplitude and time characterization data on the heart beat analysis data according to a trained heart beat classification model, to obtain primary classification information of the heart beat analysis data includes:

for the heart beat analysis data of a single lead, inputting the heart beat analysis data into the trained heart beat classification model corresponding to the single lead, performing the feature extraction and analysis of the amplitude and time characterization data with a second data amount, to obtain the primary classification information of the single lead.

Preferably, the performing feature extraction and analysis of an amplitude and time characterization data on the heart beat analysis data according to a trained heart beat classification model, to obtain primary classification information of the heart beat analysis data includes:

according to the trained heart beat classification model corresponding to each lead, performing the feature extraction and analysis of the amplitude and time characterization data on the heart beat analysis data of each lead with a third data amount, to obtain classification information of each lead; and performing classification voting decision calculation according to the classification information of each lead and lead weight reference coefficients, to obtain the primary classification information.

Preferably, the performing feature extraction and analysis of an amplitude and time characterization data on the heart beat analysis data according to a trained heart beat classification model, to obtain primary classification information of the heart beat analysis data includes:

according to a trained multi-lead synchronous correlation classification model, performing the feature extraction and analysis of a synchronous amplitude and the time characterization data on the heart beat analysis data of each lead with a fourth data amount, to obtain the primary classification information of the heart beat analysis data.

Preferably, the analyzing and evaluating a signal quality of the heart beat analysis data, and obtaining signal quality evaluation index of the heart beat analysis data includes:

extracting signals of RR intervals in the heart beat analysis data, performing second filtering processing and envelope calculation on the signals of the RR intervals to determine a signal intensity of the noise, and calculating a signal-to-noise ratio of a maximum amplitude of corresponding heart beat time sequence data to determine the signal quality evaluation index.

Preferably, the inputting the heart beat analysis data of particular heart beats in results of the primary classification information into a trained ST segment and T wave change model for identification, and determining ST segment and T wave evaluation information includes:

inputting data of the particular heart beats in the primary classification into the trained ST segment and T wave change model according to leads in turn, performing the feature extraction and analysis of the amplitude and time characterization data on the data of the particular heart beats of each lead to obtain ST segment and T wave change information of each lead, and determining the ST segment and T wave evaluation information, which is lead position information that indicates the ST segment and T wave corresponding to heart beat segment data occur change.

Preferably, wherein the performing P wave and T wave feature detection on the heart beat analysis data to determine detailed feature information includes:

performing QRS complex signal elimination processing on the heart beat analysis data, and performing third filtering on heart beat analysis data after the QRS complex signal elimination processing, performing data separation on the heart beat analysis data by an independent component analysis algorithm to obtain sequence data of each independent component, according to distribution characteristics of peak values of the sequence data of the independent component and a position of the QRS complex, selecting an independent component with the highest probability as corresponding P wave and T wave components, and determining direction and morphology features of the P wave and the T wave.

Preferably, the performing P wave and T wave feature detection on the heart beat analysis data to determine detailed feature information includes:

performing P wave and T wave signal feature extraction processing on the heart beat analysis data;

performing peak detection on signal feature data, determining a T wave detection interval between two adjacent QRS complexes, and determining a data point with a maximum amplitude in the T wave detection interval as the T wave;

determining a data point with a maximum amplitude in an interval other than the T wave detection interval between the two adjacent QRS complexes as the P wave; and determining direction and morphology features of the P wave and the T wave according to peak values and position data of the P wave and the T wave.

Preferably, the evaluating the ECG event data according to the signal quality evaluation index to generate report graphic data includes:

performing evaluation on data segments of each type of ECG event according to the signal quality evaluation index, and selecting the data segments with the highest signal quality evaluation index as typical data segments in the ECG event to generate the report graphic data.

Preferably, the method further includes:

receiving modification information of the heart beat classification information; and taking modified data as training sample data for model training in the artificial intelligence self-learning-based electrocardiogram automatic analysis method.

The artificial intelligence self-learning-based ambulatory ECG analysis method according to the embodiments of the present disclosure includes data preprocessing, heart beat feature detection, interference signal detection and heart beat classification based on deep learning methods, signal quality evaluation and lead combination, heart beat verifying, and analysis and calculation of ECG events and parameters. And it is an automatic analysis method with a complete and fast procedure through which report data is finally automatically output. The ambulatory ECG analysis method of the present disclosure may also record modification information of automatic analysis results, and collect modified data to feed back to the deep learning model for further training, thus continuously enhancing the accuracy rate of the automatic analysis method.

A second aspect of embodiments of the present disclosure provides an apparatus, the apparatus includes a memory and a processor, the memory is used for storing programs, and the processor is used for executing the first aspect and the methods in implementation manners of the first aspect.

A third aspect of embodiments of the present disclosure provides a computer program product including instructions, when the computer program product runs on a computer, the computer executes the first aspect and the methods in implementation manners of the first aspect.

A fourth aspect of embodiments of the present disclosure provides a computer-readable storage medium, the computer readable storage medium stores computer programs, and when the computer programs are executed by the processor, the first aspect and the methods in implementation manners of the first aspect are implemented.

DETAILED DESCRIPTION

Figure 1:
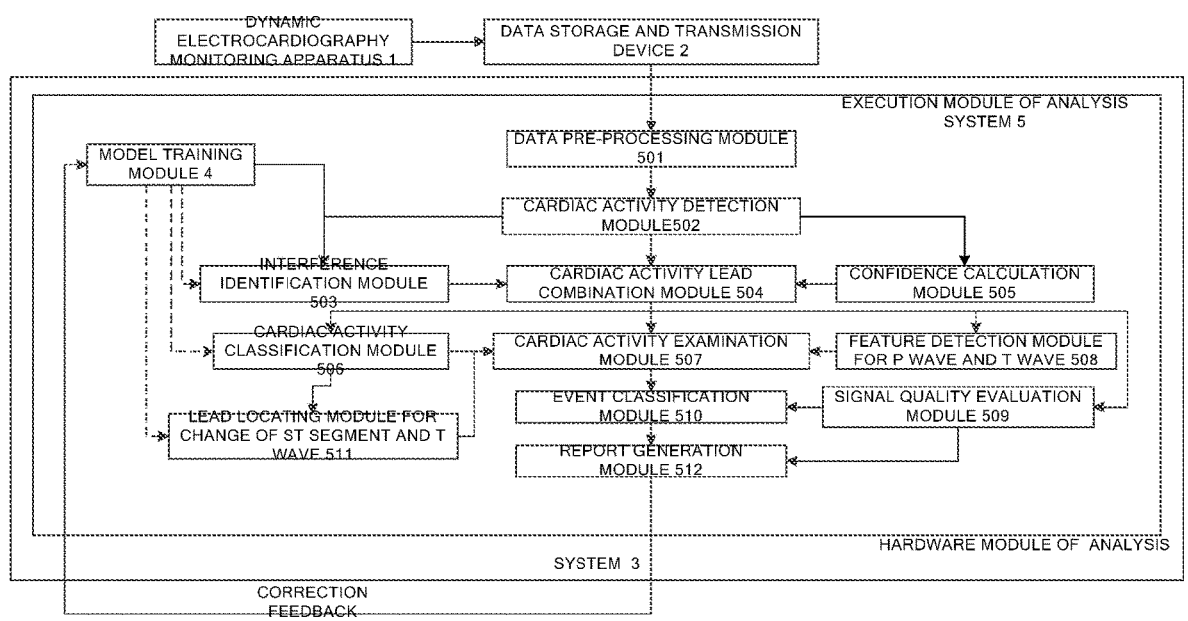
FIG. 1 is a system structure diagram illustrating an artificial intelligence self-learning-based ambulatory electrocardiogram analysis according to an embodiment of the present disclosure.

Technical solutions of the present disclosure will be further described in detail below through accompanying drawings and embodiments.

In order to facilitate understanding of the technical solutions of the present disclosure, basic principles of artificial intelligence models, especially convolutional neural network models, are first introduced.

Artificial intelligence Convolutional Neural Network (CNN) model is a supervised learning method in deep learning, which is a multi-layer network (hidden layer) connection structure that simulates a neural network. An input signal sequentially passes through each hidden layer, in which a series of complex mathematical processes (Convolution, Pooling, Regularization, prevention of over-fitting, Dropout, Activation, and general use of Rectified Linear Unit activation function) are carried out. Some features of an object to be identified are automatically abstracted layer by layer, these features are transmitted as input to a higher hidden layer for calculation until an entire signal is reconstructed by the last several full connection layers, and Softmax function is used to perform logistics regression to achieve multi-objective classification.

CNN belongs to the supervised learning method in artificial intelligence. In a training phase, the input signal is processed through multiple hidden layers to reach last full connection layers. There is an error between a classification result obtained by Softmax logical regression and a known classification result (label). One of core ideas of deep learning is to continuously minimize the error through a large number of sample iterations so as to calculate and obtain parameters for connecting neurons in each hidden layer. In this process, it is generally necessary to construct a special cost function, and quickly and effectively minimize all connection parameters in a neural network structure with complex depth (number of hidden layers) and breadth (dimension of features) by using a nonlinearly optimized gradient descent algorithm and an error back propagation (BP) algorithm.

In deep learning, images needed to be identified are input into a training model, and finally an identification result is output after the images pass through a first hidden layer, a second hidden layer and a third hidden layer. Features with different degrees of abstraction are extracted in each layer, and finally specific categories of the images are identified, such as cars, people or animals.

An algorithm model of deep learning is very complex in mathematics. Developing a complete algorithm program requires strong professional background knowledge and rich work experience. In recent years, companies such as GOOGLE®, MICROSOFT®, BAIDU®, FACEBOOK® and some famous universities (such as University of California, Berkeley, and University of Montreal in Mayada) have also successively developed and launched open source platforms for artificial intelligence development with different characteristics, helping some research and development companies in the field of deep learning to quickly master this cutting-edge technology. Among them, CAFFE™ of Berkeley and TENSORFLOW™ of GOOGLE® are currently the two most widely used framework tools.

The model of deep learning is extremely complex, and training data needed is from hundreds of thousands, millions to tens of millions, coupled with repeated loop iterations, resulting in a very large amount of nonlinear optimized calculation. For an actual project, it often takes from a dozen hours to several days or even longer to calculate by using a central processing unit of a common computer. In this case, Graphics Processing Unit (GPU) replaces it to greatly speed up the calculation. At present, GPU cards provided by Nvidia company, due to powerful graphics and computer vision computing capabilities, a large number of computing database such as linear algebra, and supporting of parallel processing, may meet the computing of various methods with deep learning needs, and becomes a basic hardware for high-performance training and inference of current artificial intelligence.

An artificial intelligence self-learning-based ambulatory electrocardiogram analysis method of the present disclosure is implemented based on the CNN model.

The artificial intelligence self-learning-based ambulatory electrocardiogram analysis method provided by the embodiments of the present disclosure is implemented based on a system architecture shown in FIG. 1. The system architecture includes an ECG monitoring device 1, a data storage and transmission apparatus 2, an analysis system hardware module 3, a model training module 4 and an analysis system execution module 5. The analysis system execution module 5 specifically includes a data preprocessing module 501, a heart beat detection module 502, an interference identification module 503, a lead heart beat combination module 504, a confidence calculation module 505, a heart beat classification module 506, a heart beat verification module 507, a P wave and T wave feature detection module 508, a signal quality evaluation module 509, an event classification module 510, an ST segment and T wave change lead location module 511 and a report generation module 512. A process of the artificial intelligence self-learning-based ambulatory electrocardiogram analysis is realized through the analysis system hardware module 3, the model training module 4 and the analysis system execution module 5 in the system architecture.

Figure 2:
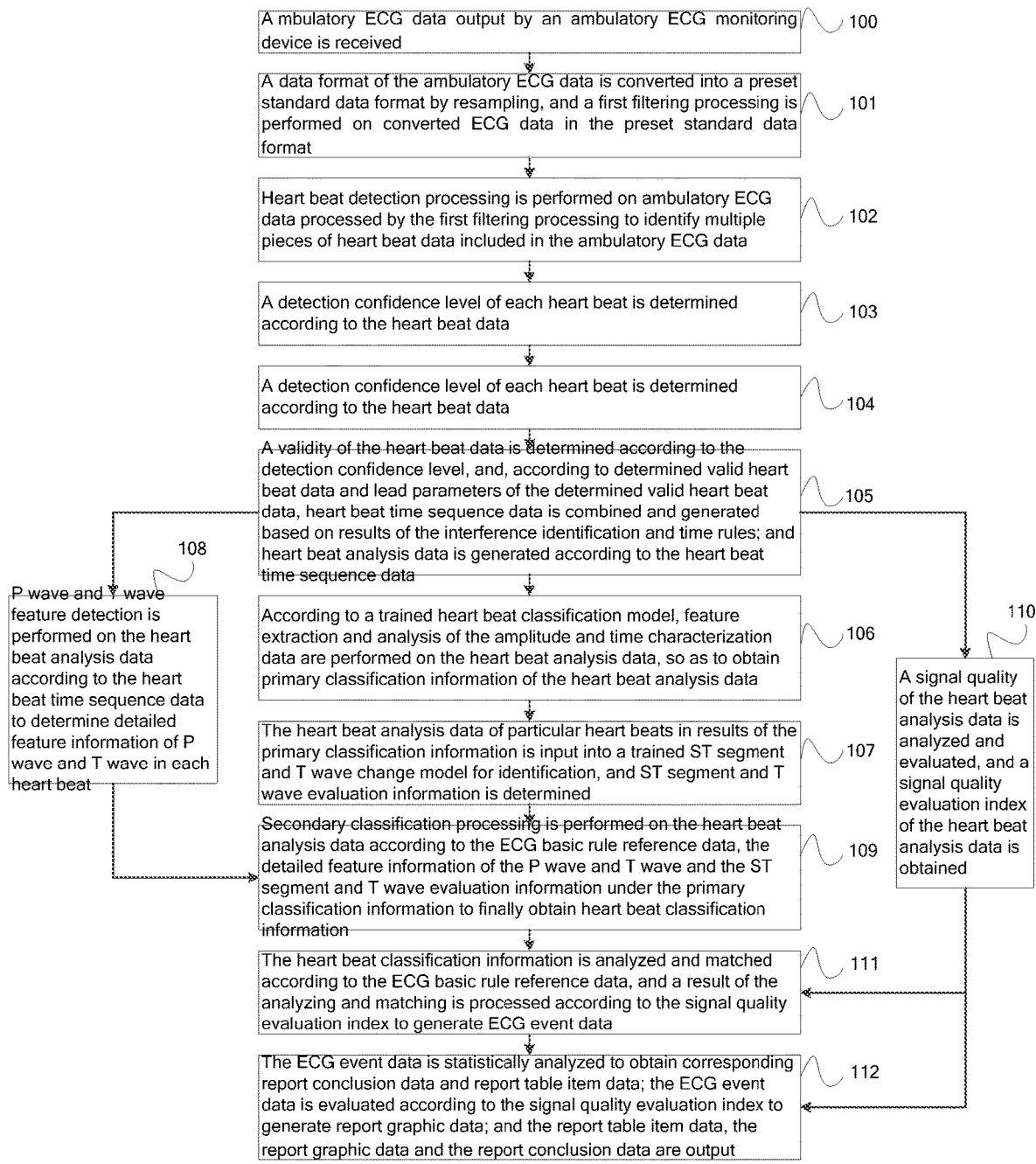
FIG. 2 is a flowchart illustrating an artificial intelligence self-learning-based ambulatory electrocardiogram analysis method according to an embodiment of the present disclosure.

Based on the system architecture of FIG. 1 and in combination with FIG. 2, the artificial intelligence self-learning-based ambulatory electrocardiogram analysis method of the present disclosure will be described below.

The method includes the following steps:

Step 100: ambulatory ECG data output by an ambulatory ECG monitoring device is received.

Specifically, electrical signals of the ambulatory ECG are converted into digital signals by the ambulatory ECG monitoring device for output, which may be time sequence data measured, collected and output by a single-lead or multi-lead ambulatory ECG device, or single-lead or multi-lead ambulatory ECG data obtained through a database or other file manners. Original data is stored by the data storage and transmission apparatus, and it may be transmitted to the analysis system hardware module through WIFI, BLUETOOTH®, USB, 3G/4G/5G mobile communication networks, Internet of Things and other means, and input into the analysis system execution module as input signals.

As ambulatory ECG time sequence data for recording ambulatory ECG graphics, due to differences in the acquisition of analog circuits, filters, and sample rates of ambulatory ECG devices from different device manufacturers, the generated ambulatory ECG time sequence data has great differences in lead labels, data encoding formats, gains, precision, data length per second, baseline positions and the like, data preprocessing needs to be carried out. All input ambulatory ECG time sequence data is processed uniformly according to requirements of the analysis process of the present disclosure and stored according to a preset standard data format. The preset standard data format refers to a data format may support data identification for the whole process of data processing.

Step 101: a data format of the ambulatory ECG data is converted into a preset standard data format by resampling, and a first filtering processing is performed on converted ECG data in the preset standard data format.

Specifically, the data preprocessing module executes the format adaptive to be read, resampling, filtering, and storing in a standard data format for the ambulatory ECG data. The format of the ambulatory ECG data adaptive to be read, has different readings implemented for different devices, and a baseline needs to be adjusted and the ambulatory ECG data needs to be converted into millivolt data according to a gain after reading. The ambulatory ECG data is resampled to convert the data at a sample frequency that may be processed by the whole process. Then, high frequency, low-frequency noise interference and baseline drift are eliminated by the filtering to improve the accuracy of artificial intelligence analysis. The processed ambulatory ECG data is stored in the preset standard data format.

Through this step, differences in the lead, sample frequency and transmission data format used by different ambulatory ECG devices may be eliminated, and the high frequency, low-frequency noise interference and baseline drift may be removed by digital signal filtering.

In a specific example, a resample frequency may be 200 Hz to ensure that a data length of each fixed time range is consistent in calculation, training and reasoning, so that a relatively satisfactory analysis result may be obtained without excessively increasing the complexity and time of calculation and training. Certainly, as sample rates of ECG devices themselves gradually increase, GPU computing performance continues to rise and the cost decreases, and artificial intelligence algorithms continue to innovate and optimize, the sample frequency may further be improved.

The digital signal filtering may adopt a high-pass filter, low-pass filter and median filtering, respectively, to eliminate power line noise, electromyogram interferences and baseline drift interferences, so as to avoid the impact on subsequent analysis.

More specifically, a low-pass, high-pass Butterworth filter may be used for zero-phase shift filtering to eliminate the baseline drift and high-frequency interference, and to retain effective ECG signals. The median filtering may replace an amplitude of a sequence in a center of a window with a median of voltage amplitudes of data points in a sliding window of a preset length of time, therefore a low-frequency baseline drift may be eliminated.

Step 102: heart beat detection processing is performed on the ambulatory ECG data processed by the first filtering processing to identify multiple pieces of heart beat data included in the ambulatory ECG data.

Each piece of heart beat data corresponds to a heart beat cycle, including amplitude data and starting-ending time data of corresponding P wave, QRS complex and T wave. Heart beat detection performed by the heart beat detection module includes QRS complex detection, P wave and T wave detection. The QRS complex detection includes two processes: one is signal processing, extracting characteristic frequency bands of the QRS complex from the ECG data processed by the first filtering processing, and the other is to determine occurrence time of the QRS complex by setting a reasonable threshold. The ECG normally includes components of P wave, QRS complex and T wave, and a noise component. Generally, the QRS complex has a frequency range of 5 Hz to 20 Hz, so signals of the QRS complex may be extracted by a band-pass filter in this range. However, frequency bands of the P wave, the T wave, and the noise are partially overlapped with the QRS complex, so signals of non QRS complex may not be completely removed by the signal processing. Therefore, it is necessary to extract a position of the QRS complex from a signal envelope by setting a reasonable threshold. The specific detection process is a process based on peak detection. Threshold judgment is sequentially performed for each peak in the signals, and when the threshold is exceeded, a judgment process of the QRS complex is executed to detect more features, such as RR interval, morphology, etc.

Due to an instability characteristic of heart beat signals in time domain during a process of long-term wearing and recording of the ambulatory ECG, the amplitude and frequency of the heart beat signals constantly change, and this characteristic is stronger in a disease state. When the threshold is set, a threshold adjustment needs to be dynamically performed according to the change of data characteristics in the time domain. In order to improve the accuracy and positive rate of the detection, the QRS complex detection is mostly carried out by using a double amplitude threshold combined with a time threshold. A high threshold has a high positive rate and a low threshold has a high sensitivity rate. When the RR interval exceeds a certain time (time threshold), the low threshold is used for detection to reduce missed detection. However, the low threshold is susceptible to T wave and electromyography noise due to its low threshold, which is easy to cause excessive detection. Therefore, the high threshold is preferred for detection.

There are lead parameters available for heart beat data of different leads to characterize which lead the heart beat data belongs to. Therefore, in this step, the lead parameters of the heart beat data are also determined.

Step 103: a detection confidence level of each heart beat is determined according to the heart beat data.

During a process of the heart beat detection, the confidence calculation module may provide an estimation value of the detection confidence level for the QRS complex according to an amplitude ratio between the QRS complex and noise signals within the RR interval.

Step 104: interference identification is performed on the heart beat data according to a trained interference identification two-classification model to obtain whether there is interference noise in the heart beat data with a probability value for judging the interference noise.

Since ambulatory ECG detection is susceptible to interference caused by various influences in a long-time recording process, resulting in invalid or inaccurate acquired data, which may not correctly reflect condition of participants and increases the difficulty and workload of doctors in diagnosis. In addition, interference data is also a main factor that causes intelligent analysis tools unable to work effectively. Therefore, it is particularly important to minimize external signal interference. For a long time, in the computer automatic analysis method for the ambulatory ECG, an accurate identification for the interference signals has not been satisfactorily solved, resulting in an overall accuracy of computer analysis algorithms of the ambulatory ECG is not high.

This step is based on an end-to-end two-classification identification model with deep learning algorithms as its core, and it has characteristics of high precision and strong generalization performance, and it may effectively solve disturbance problems caused by main disturbance sources such as electrode peeling off, exercise interference noise and electrostatic interference noise, and thus, the problem of poor identification caused by various and irregular disturbance data in traditional algorithms is overcome.

Wherein the process for interference identification is performed by the interference identification module, and it may include steps as below:

step A: using the interference identification two-classification model for the heart beat data to identify interference;

step B: identifying a data segment with a heart beat interval greater than or equal to a preset interval determination threshold in the heart beat data;

step C: performing a judgment of signal abnormality on the data segment with the heart beat interval greater than or equal to the preset interval determination threshold to determine whether the data segment is an abnormal signal;

wherein the identification of the abnormal signal includes whether there are electrode peeling off, low voltage, etc.;

step D: if the data segment is not an abnormal signal, according to a set time value, a starting data point and an ending data point of sliding sampling in the data segment are determined with a preset time width, and the sliding sampling is performed on the data segment from the starting data point until the ending data point to obtain multiple sample data segments; and step E: performing the process for interference identification on each of the multiple sample data segments.

The above steps A-E will be described in a specific example. The heart beat data of each lead is cut and sampled with a first data amount, and then input into the interference identification two-classification model, respectively, for classification, and an interference identification result and a probability value corresponding to such result are obtained. For the heart beat data with the heart beat interval greater than or equal to 2 seconds, whether it is signal overflow, low voltage, electrode peeling off is first judged. If it is not in the above case, sliding sampling without overlapping is continuously performed from a left heart beat to the right with the first data amount for identification.

The input may be the first data amount of heart beat data of any lead, the interference identification two-classification model is adopted for classification, and a classification result of whether the heart beat data is the interference or not is directly output. The result is obtained quickly, the accuracy is high, the stability performance is good, and effective and high-quality data may be provided for subsequent analysis.

The above-mentioned structure of the interference identification two-classification model is an end-to-end two-classification identification system inspired and constructed by artificial intelligence deep learning CNN models such as LeNet-5 and AlexNet.

For the training of the model, nearly 4 million accurately labeled data segments from 300,000 patients are used. Labeling is divided into two categories: normal ECG signals or ECG signal fragments with obvious interference. The segments are labeled by custom-developed tools, and then interference fragment information is saved in a customized standard data format.

In the training process, two GPU servers are used for dozens of round-robin training. In a specific example, for a segment D [300] with a sample rate of 200 Hz and a data length of 300 ECG voltage values (millivolts), input data is: InputData (i, j), wherein i is a i-th lead, and j is a j-th segment of the i-th lead. All input data is randomly scattered before training, which ensures convergence of the training process. At the same time, collection of too many samples from the ECG data of a same patient is controlled, improving the generalization ability of the model, that is, an accuracy rate in a real scene. After the training converges, one million pieces of independent test data are used for testing, and the accuracy rate may reach 99.3%. Additionally, specific test data is shown in Table 1 below.

TABLE 1

|  | Interference | Normal |
|---|---|---|
| Sensitivity | 99.14% | 99.32% |
| Positive Predictivity | 96.44% | 99.84% |

Interference data is often caused by external disturbance factors, mainly including electrode peeling off, low voltage, electrostatic interference and motion interference. Not only interference data generated by different disturbance sources is different, but also interference data generated by a same disturbance source is diverse. At the same time, considering that although the diversity of interference data is widely distributed, the difference with normal data is very large, so the diversity is ensured as much as possible when collecting interference training data. Furthermore, moving window sliding sampling is adopted to increase the diversity of interference data as much as possible, so as to make the model robust to interference data. Even if interference data in the future is different from any previous interference, with comparison to normal data, its similarity with interference is greater than normal data, thus enhancing the ability of the model to identify interference data.

Figure 3:
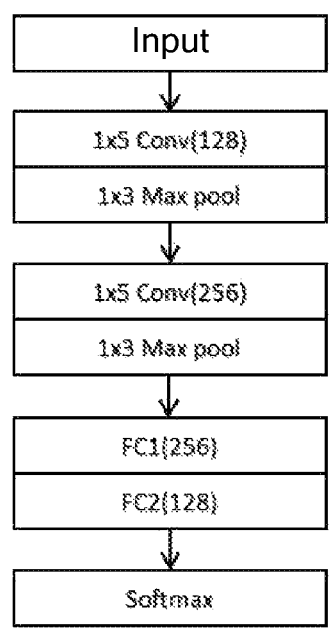
FIG. 3 is a schematic diagram illustrating an interference identification two-classification model according to an embodiment of the present disclosure.

The interference identification two-classification model adopted in this step may be shown in FIG. 3. The network first uses two convolutional layers, the convolution kernel in size is 1×5, and each layer is followed by a maximum pooling. The number of the convolution kernel starts from 128, and the number of the convolution kernel doubles every time passing a maximum pooling layer. The convolutional layers are followed by two full connection layers and a Softmax classifier. Since the classification number of the model is two, Softmax has two output units that correspond to corresponding categories in turn, and uses cross entropy as the cost function.

Step 105: a validity of the heart beat data is determined according to the detection confidence level, and, according to determined valid heart beat data and lead parameters of the determined valid heart beat data, heart beat time sequence data is combined and generated based on results of the interference identification and time rules; and heart beat analysis data is generated according to the heart beat time sequence data.

Due to the complexity of the ECG signals and the fact that each lead may be affected by different degrees of interference, there may be excessive detection and missed detection when the heart beat detection depends on a single lead. Time characterization data of heart beat results detected by different leads is not aligned. Therefore, the heart beat data of all leads needs to be combined according to results of the interference identification and time rules to generate complete heart beat time sequence data, and the time characterization data of the heart beat data of all leads is unified. The time characterization data is used to represent time information of each data point on a time axis of ECG data signals. In the subsequent analysis and calculation, according to the unified heart beat time sequence data, the heart beat data of each lead may be cut with the preset threshold, so as to generate the heart beat analysis data of each lead required for specific analysis.

Before the above mentioned heart beat data of each lead is combined, the validity of the heart beat data needs to be determined according to the detection confidence level obtained in step 102.

Specifically, the process of combining the heart beat data performed by the lead heart beat combination module is as follows: a time characterization data combination of the heart beat data of different leads is obtained according to a refractory period of ECG basic rule reference data, the heart beat data with a large deviation is discarded, the time characterization data combination is voted to generate a position of a combined heart beat, and the position of the combined heart beat is added to the combined heart beat time sequence. It returns to a next group of heart beat data to be processed, and repeats until combination of all heart beat data is finished.

The refractory period of the ECG activities may preferably be between 200 ms and 280 ms. The time characterization data combination of the heart beat data of different leads obtained should meet the following conditions: each lead in the time characterization data combination of the heart beat data includes at most the time characterization data of one piece of heart beat data. When the time characterization data combination of the heart beat data is voted on, it is determined by a percentage of a number of leads with detected heart beat data in a number of effective leads. If a position of the time characterization data of the heart beat data corresponding to a lead is a low voltage segment, an interference segment and electrode peeling off, the lead is considered as an invalid lead for the heart beat data. The specific position of the combined heart beat may be calculated and obtained by using an average value of the time characterization data of the heart beat data. During the combining process, the refractory period is set in this method to avoid erroneous combining.

In this step, the unified heart beat time sequence data is output through combining. This step may simultaneously lower excessive detection and missed detection rates of the heart beat, and effectively improve the sensitivity and positive predictivity of the heart beat detection.

Step 106: according to a trained heart beat classification model, feature extraction and analysis of the amplitude and time characterization data are performed on the heart beat analysis data, so as to obtain primary classification information of the heart beat analysis data.

Since there are differences in signal measurement, acquisition, output lead data and other aspects for different ambulatory ECG devices, and actual application scenes are different, a simple single-lead classification method or a multi-lead classification method may be adopted according to specific situations for the heart beat classification method performed by the heart beat classification module of the present disclosure. The multi-lead classification method includes lead voting decision classification method and lead synchronous correlation classification method. The lead voting decision classification method is a voting decision method that leads are independently classified based on the heart beat analysis data of each lead, and then voting results are merged to determine a classification result. The lead synchronous correlation classification method is a method for synchronous correlation and analysis of the heart beat analysis data of each lead. The single-lead classification method is to directly use a corresponding lead model to classify the heart beat analysis data of a single-lead device, and there is no voting decision process. The classification methods mentioned-above will be respectively described in the following.

The single-lead classification method includes:
according to the heart beat time sequence data, cutting is performed on the heart beat data of the single lead with a second data amount to generate the heart beat analysis data of the single lead, and the heart beat analysis data of the single lead is input into the trained heart beat classification model corresponding to such lead for the feature extraction and analysis of the amplitude and time characterization data, so as to obtain the primary classification information of the single lead.

The lead voting decision classification method may include:
firstly, according to the heart beat time sequence data, cutting is performed on the heart beat data of each lead with a third data amount to generate the heart beat analysis data of each lead;
secondly, according to the trained heart beat classification model corresponding to each lead, the feature extraction and analysis of the amplitude and time characterization data are performed on the heart beat analysis data of each lead, so as to obtain classification information of each lead; and
thirdly, classification voting decision calculation is performed according to the classification information of each lead and lead weight reference coefficients, so as to obtain the primary classification information. Specifically, the lead weight reference coefficients are voting weight coefficients of each lead for different heart beat classifications based on the Bayesian statistical analysis of the ECG data.

The lead synchronous correlation classification method may include:
according to the heart beat time sequence data, cutting is performed on the heart beat data of each lead with a fourth data amount to generate the heart beat analysis data of each lead; and then, according to a trained multi-lead synchronous correlation classification model, the feature extraction and analysis of a synchronous amplitude and time characterization data are performed on the heart beat analysis data of each lead, so as to obtain the primary classification information of the heart beat analysis data.

An input of the synchronous correlation classification method of the heart beat data is data of all leads of the ambulatory ECG device, and data points with a same position and a certain length of each lead are intercepted according to unified heart beat positions of the heart beat analysis data, and are synchronously delivered to a trained artificial intelligence deep learning model for calculation and analysis, and an output is that an accurate heart beat classification in which ECG signal characteristics of all lead and heart rhythm characteristics correlated with the heart beat in time are comprehensively considered at each heart beat position.

In this method, it is fully considered the data of different leads of the ambulatory ECG is, actually measuring information flow of heart electrical signals transmitted in the directions of different ECG axis vectors, and multi-dimensional digital characteristics transmitted by the ambulatory ECG signal in time and space are comprehensively analyzed, so it effectively overcomes the defect that the traditional method only relies on independent analyses of a single lead, and then results are accumulated to conduct some statistical voting methods through which classification errors are easily obtained, and greatly improves the accuracy of the heart beat classification.

The heart beat classification model in this step is obtained by training 17 million data samples of 300,000 patients in a training set. These samples are generated by accurately labeling the data according to requirements of ambulatory ECG analysis and diagnosis. Labeling is mainly for common arrhythmias, conduction block, ST segment and T wave changes, which may meet model training in different application scenes. Specifically, labeled information is stored in a preset standard data format. In the preprocessing of training data, in order to increase the generalization ability of the model, small sliding is made for a classification with a small sample size to expand the data. Specifically, the data is moved 2 times based on each heart beat according to a certain step (such as 10-50 data points), so that the data may be increased by 2 times, and the recognition accuracy of classification samples with a small amount of data is improved. The generalization ability has also been verified to be improved from the actual result.

In an actual training process, two GPU servers are used for dozens of round-robin training. After the training converges, 5 million pieces of independent test data are used for testing, and the accuracy rate may reach 91.92%.

An interception length of the training data may be from 1 second to 10 seconds. For example, a sample rate is 200 Hz, a sample length is 2.5 s, an obtained data length is a segment D[500] of 500 ECG voltage values (millivolts), and input data is: InputData (i, j), wherein i is a i-th lead, and j is a j-th segment of the i-th lead. All input data is randomly scattered before training, which ensures convergence of the training process. At the same time, collection of too many samples from the ECG data of a same patient is limited, which improves the generalization ability of the model, that is, an accuracy rate in a real scene. During the training, segment data D corresponding to all leads is synchronously input, and lead data of multiple spatial dimensions (different ECG axis vectors) of each time position is synchronously learned according to a multi-channel analysis method of image analysis, so that a more accurate classification result than a conventional algorithm is obtained.

Figure 4:
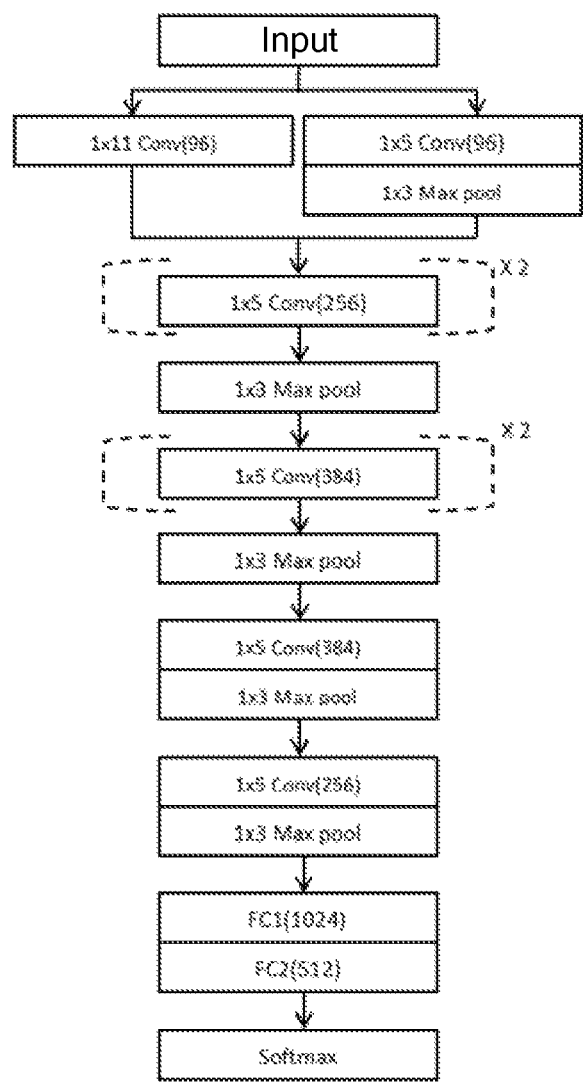
FIG. 4 is a schematic diagram illustrating a heart beat classification model according to an embodiment of the present disclosure.

As shown in FIG. 4, it is the heart beat classification model adopted in this step may, and it specifically may be an end-to-end multi-label classification model inspired by CNN models based on artificial intelligence deep learning such as AlexNet, VGG16, Inception. Specifically, the network of this model is a seven-layer convolution network, and each convolution is followed by an activation function. A first layer is a convolution layer having two different scales, followed by six convolution layers. The number of convolution kernels of the seven-layer convolution are 96, 256, 256, 384, 384, 384 and 256, respectively. Except for the convolution kernel of the first layer, which has two scales of 5 and 11, the convolution kernels of other layers have a scale of 5. Third, fifth, sixth and seventh convolution layers are followed by a pooling layer. Finally, two full connection layers follow.

Step 107: the heart beat analysis data of particular heart beats in results of the primary classification information is input into a trained ST segment and T wave change model for identification, and ST segment and T wave evaluation information is determined.

Wherein, the ST segment and T wave evaluation information is lead position information that the ST segment and T wave corresponding to the heart beat analysis data is changed. In clinical diagnosis, changes for the ST segment and T wave are required to be located to a specific lead.

Wherein, the data of the particular heart beats of the primary classification information refers to the heart beat analysis data including sinus heart beat (N) and other heart beat types that may include ST segment changes.

Figure 6:
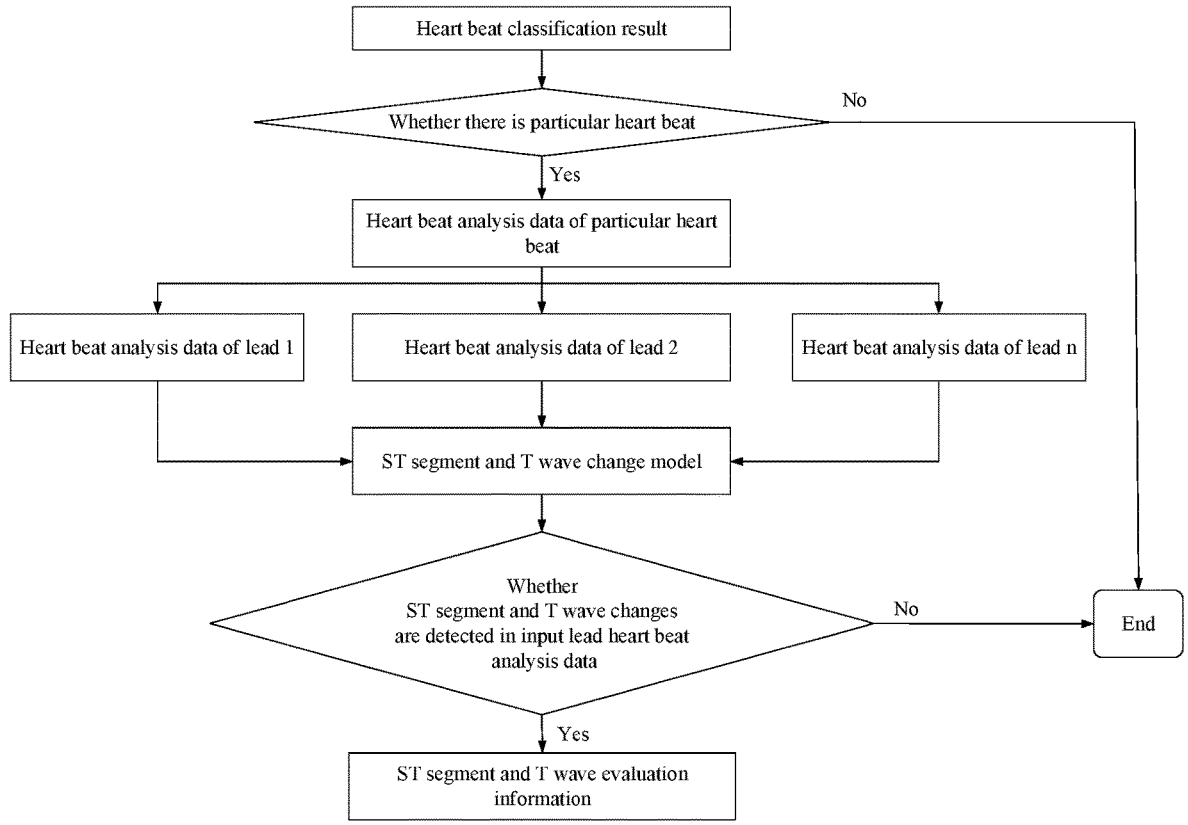
FIG. 6 is a flowchart illustrating a ST segment and T wave change location analysis according to an embodiment of the present disclosure.

The data of particular heart beats in the primary classification information is put into a trained artificial intelligence deep learning model for identifying the ST segment and T wave changes according to each lead in turn by the ST segment and T wave change lead location module, and calculation and analysis is performed. An output result indicates whether features of lead segments conform to the conclusion that ST segment and T wave change, so that the information of leads where the ST segment and T wave changes occur may be determined, that is, the ST segment and T wave evaluation information. The specific method may be as follows: the heart beat analysis data of each lead, which is the sinus heart beat in the primary classification information, is put into the ST segment and T wave change model, and the sinus heart beat data is identified and judged one by one, so as to determine whether the sinus heart beat has characteristics of ST segment and T wave change and specific lead position information that the change occurs, and the ST segment and T wave evaluation information is determined. The schematic diagram of such process may be shown in FIG. 6.

A proportion of the heart beat with the ST segment and T wave changes in all heart beats is relatively low. In order to take into account a diversity of the training data and a balance of the amount of data in each category, a ratio of training data without ST segment and T wave changes and with ST segment and T wave changes is selected about 2:1, which ensures the good generalization ability of the model in the process of classification and avoid to appear a tendency of a category accounting for a relatively large proportion in the training data. Forms of the heart beat are diverse and different individuals show different forms, therefore, in order to make the model estimate distribution of each classification well and extract features effectively, training samples are collected from individuals of different ages, weights, genders and residential areas. In addition, since the ECG data of a single individual in a same time period is often highly similar, in order to avoid over-learning, when acquiring the data of the single individual, a small number of samples in different time periods are randomly selected from all the data. Finally, due to characteristics that the forms of the heart beat of patients have large differences between individuals and high similarity within the individual, different patients are divided into different data sets when dividing training sets and test sets, so as to prevent the data of a same individual from appearing in the training sets and test sets at the same time. Therefore, test results of the obtained model are closest to real application scenes, ensuring the reliability and universality of the model.

Figure 5:
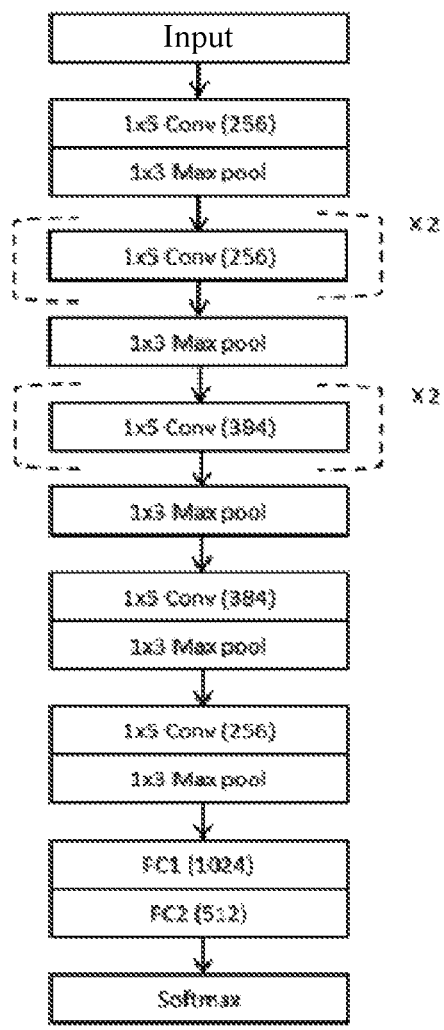
FIG. 5 is a schematic diagram illustrating a ST segment and T wave change model according to an embodiment of the present disclosure.

The ST segment and T wave change model adopted in this step may be as shown in FIG. 5, and it may be an end-to-end classification model inspired by CNN models based on artificial intelligence deep learning such as AlexNet and VGG16. Specifically, the model is a seven-layer network, which includes seven layers of convolution, five layers of pooling and two layers of full connection. A convolution kernel used in all layers of convolution is 1×5, and the number of filters for each layer of the convolution is different. The number of the filters for a first layer of convolution is 96; a second layer of convolution and a third layer of convolution are used together, and the number of the filters is 256; a fourth layer of convolution and a fifth layer of convolution are used together, and the number of the filters is 384; the number of the filters for a sixth layer of convolution is 384; the number of the filters for a seventh layer of convolution is 256. The first, third, fifth, sixth and seventh layers of convolution are followed by the layers of pooling, and then, the two layers of full connection follow. Finally, a Softmax classifier is used to divide the results into two categories. In order to increase the nonlinearity of the model and extract the features of high dimensions of the data, the mode that two layers of convolution are used together is adopted.

Step 108: P wave and T wave feature detection is performed on the heart beat analysis data according to the heart beat time sequence data to determine detailed feature information of P wave and T wave in each heart beat.

Wherein, the detailed feature information includes data of amplitudes, directions, forms and starting-ending time. In the analysis of the heart beat signals, the features of the P wave, T wave and QRS complex are also important basis for the ECG analysis.

In the P wave and T wave feature detection module, the features of the P wave, T wave, and QRS complex are extracted by calculating a position of a segmentation point of the QRS complex and a position of a segmentation point of the P wave and the T wave, which may be realized by QRS complex segmentation point detection, single-lead PT detection algorithms and multi-lead PT detection algorithms, respectively.

The QRS complex segmentation point detection: according to a segment power maximum point and starting and ending points of the QRS complex provided by QRS complex detection algorithms, a R point, R' point, S point and S' point of the QRS complex in a single lead are searched. When there is multi-lead data, a median of each segmentation point is calculated as the final position of the segmentation point.

The single-lead P wave and T wave detection algorithms: compared with the QRS complex, the P wave and T wave are relatively low in amplitude and gentle in signal, and easy to be submerged in the low-frequency noise, which is a difficulty in the detection. In this method, according to a result of the QRS complex detection, third filtering is performed on the signals by using a low-pass filter to increase relative amplitudes of the P and T waves after eliminating an influence of the QRS complex on low-frequency bands. The T wave is then searched between two QRS complexes by the peak detection. Since the T wave is a wave complex generated by ventricular repolarization, there is a definite time-locked relationship between the T wave and the QRS complex. Based on the detected QRS complex, a midpoint of interval between each QRS complex and next QRS complex (e.g., limited to a range from 400 ms to 600 ms following a first QRS complex) is taken as an ending point of the T wave detection, and the largest peak in this range is taken as the T wave. Then a peak with the largest amplitude in remaining peaks is selected as the P wave. At the same time, direction and morphology features of the P wave and the T wave are determined according to peak values and position data of the P wave and the T wave. Preferably, a cut-off frequency of the low-pass filtering is set from 10 Hz to 30 Hz.

The multi-lead P wave and T wave detection algorithms: in the case of multiple leads, each wave in a heart beat is generated at same time, but has different space distribution, while the noise has different time and space distribution, therefore the P and T waves may be detected by tracing algorithms. Firstly, QRS complex elimination processing is performed on the signals and third filtering is performed on the signals by using a low-pass filter to remove interference, and then individual independent components of an original waveform are calculated by an independent component analysis algorithm. In separated individual independent components, corresponding components are selected as P wave and T wave signals according to distribution characteristics of peaks and the position of the QRS complex, and the direction and morphology features of the P wave and the T wave are determined.

Step 109: secondary classification processing is performed on the heart beat analysis data according to the ECG basic rule reference data, the detailed feature information of the P wave and T wave and the ST segment and T wave evaluation information under the primary classification information to finally obtain heart beat classification information.

The ECG basic rule reference data such as a minimum time interval between two heart beats, a minimum interval between the P wave and R wave, is generated according to the description of basic rules of cardiomyocytes electrophysiological activities and ECG clinical diagnosis in authoritative ECG textbooks, and which is used for subdividing the primary classification information after classification of the heart beat mainly based on the RR interval between the heart beats and a medical significance of different heart beat signals on each lead. According to the ECG basic rule reference data combined with classification and identification of a certain number of continuous heart beats and the detailed feature information of the P wave and T wave, a classification of ventricular heart beats is divided into more detailed heart beat classifications by the heart beat verification module, including ventricular premature beat (V), ventricular escape beat (VE), ventricular tachycardia beat (VT), and supraventricular heart beats are subdivided into supraventricular premature beat (S), atrial escape beat (SE), junctional escape beat (JE) and atrial tachycardia beat (AT), etc.

In addition, through the secondary classification processing, erroneous classification identification that does not conform to the ECG basic rule reference data in the primary classification may also be corrected. The subdivided heart beat classifications are pattern matched according to the ECG basic rule reference data, classification identification, which does not conform to the ECG basic rule reference data is found, and corrected to a reasonable classification according to the RR interval and classification labels before and after.

Specifically, after the secondary classification processing, a variety of heart beat classifications may be output, such as: normal sinus heart beat (N), complete right bundle branch block (N_CRB), complete left bundle branch block (N_CLB), intraventricular block (N_VB), first degree atrioventricular block (N_B1), pre-excitation syndrome (N_PS), ventricular premature beat (V), ventricular escape beat (VE), ventricular tachycardia beat (VT), supraventricular premature beat (S), atrial escape beat (SE), junctional escape beat (JE), atrial tachycardia beat (AT), atrial flutter/atrial fibrillation (AF) and artifact (A).

The calculation of basic heart rate parameters may also be completed through this step. The calculated basic heart rate parameters include the RR interval, heart rate, QT time, QTc time and other parameters.

Step 110: a signal quality of the heart beat analysis data is analyzed and evaluated, and a signal quality evaluation index of the heart beat analysis data is obtained.

The signal quality evaluation module extracts RR interval signals in the heart beat analysis data, performs second filtering processing and envelope calculation on the RR interval signals to determine a noise signal intensity, and calculates a signal-to-noise ratio of a maximum amplitude of corresponding heart beat time sequence data to determine the signal quality evaluation index. The following steps may be included:

step A: position information and width information of the QRS complex in the heart beat analysis data are extracted;

step B: RR interval signals within RR interval between two adjacent QRS complex signals are extracted;

step C: filtering the RR interval signals is performed, and an envelope calculation is performed on filtered signals to obtain an average power of noise signals in the RR interval; wherein the average power of the noise signals in the RR interval is an average of an envelope amplitude in the RR interval; and step D: the signal quality evaluation index is obtained according to the average power of the noise signals and a power of the signals of the QRS complex.

Further, the signal quality evaluation index may be characterized by a noise level in the RR interval respect to the QRS complex, and it is calculated based on the power of the QRS complex and the average power of the noise signals.

The signal quality evaluation index is expressed by the formula:

$$SNR(i) = \frac{S_i}{\sum N_{i,t} \div T};$$

wherein Si is an amplitude of a i-th QRS complex, Ni,t is an amplitude of a t-th sample point in a i-th RR interval, and T is a length of the RR interval.

Step 111: the heart beat classification information is analyzed and matched according to the ECG basic rule reference data, and a result of the analyzing and matching is processed according to the signal quality evaluation index to generate ECG event data.

Specifically, the event classification module performs pattern matching according to results of the secondary classification for the heart beat and the ECG basic rule reference data, and obtains the ECG event data in the heart beat data in combination with the signal quality evaluation index.

Specifically, the event classification module may classify the following typical ECG events corresponding to the ECG event data, including but not limited to:

supraventricular premature beat
pairs of supraventricular premature beat
supraventricular premature beat bigeminy
supraventricular premature beat trigeminy
atrial escape beat
atrial escape rhythm
junctional escape beat
junctional escape rhythm
non-paroxysmal superventricular tachycardia
fastest superventricular tachycardia
longest superventricular tachycardia
superventricular tachycardia
short superventricular tachycardia
atrial flutter-atrial fibrillation
ventricular premature beat
pairs of ventricular premature beat
ventricular premature beat bigeminy
ventricular premature beat trigeminy
ventricular escape beat
ventricular escape rhythm
acelerated idioventricular rhythm
fastet ventricular tachycardia
longet ventricular tachycardia
ventricular tachycardia
short ventricular tachycardia
second-degree type I sinoatrial block
second-degree type II sinoatrial block
first-degree atrioventricular block
second-degree type I atrioventricular block
second-degree type II atrioventricular block
second-degree type II (2:1)atrioventricular block
high-degree atrioventricular block
complete left bundle branch block
complete right bundle branch block
intraventricular block
pre-excitation syndrome
ST segment and T wave change
longest RR interval Step 112: the ECG event data is statistically analyzed to obtain corresponding report conclusion data and report table item data; the ECG event data is evaluated according to the signal quality evaluation index to generate report graphic data; and the report table item data, the report graphic data and the report conclusion data are output.

Specifically, referring to the signal quality evaluation index, the report generation module removes untrusted events from the ECG event data, calculates various heart rate parameters, counts the number and occurrence time of events, etc., and obtains the report conclusion data and the report table item data.

Specific calculation of the heart rate parameters includes calculation of an average heart rate, a maximum heart rate and a minimum heart rate, etc. When calculating the maximum and minimum heart rates, a fixed-length segment is taken as a statistical unit, and whole process scanning and statistical comparison are performed on the heart beats one by one. The length of the segment is generally 8-10 seconds, and it may be freely set as required. When calculating the heart rate, different statistical calculation methods for heart beat types are adopted for ECG dominated by sinus heart rate and ECG dominated by ectopic heart rate. When calculating the maximum and minimum heart rates, only the sinus heart beat is calculated for the ECG dominated by sinus heart rate. For ECG dominated by the atrial flutter/atrial fibrillation, only the atrial flutter/atrial fibrillation and sinus heart beats are calculated. For ECG dominated by other non atrial flutter/atrial fibrillation ectopic heart beats, all types of heart beats except the artifact are involved in the calculation.

Specifically, the report generation module may calculate the following heart rate parameters:

time:
  total length of time of monitoring
  total length of time of interference
  effective length of time
  starting-ending time
heart rate:
  average heart rate
  maximum heart rate and occurrence time
  minimum heart rate and occurrence time
  total number of heart beats
  percentage of abnormal heart beats in total heart beats
  percentage of atrial flutter-atrial fibrillation in total heart beats
heart rate variability:
  standard deviation between sinus beats
  mean standard deviation of RR interval
RR interval:
  occurrence times of long RR interval (1.5-2.0 s)
  occurrence times of 3s >long RR interval >2.0s
  occurrence times of 5s >long RR interval >3s occurrence times of long RR interval >5s
longest RR interval (S) and occurrence time
As well as numbers of various ECG events, duration, or occurrence time, etc.

Quality evaluation is performed on the ECG event data according to the signal quality evaluation index, event segments with the highest data signal quality are selected, meanwhile, a number of event types included in the segments is analyzed, the most representative segment is preferentially selected, a starting position of the segment is preferred to ensure that an event heart beat is located in a middle of the selected segment as far as possible, and the report graphic data is generated.

In a preferred embodiment, selection rules of the ECG events may be specifically described as follows.

A single segment is selected for general ECG events. When the heart rate of a first heart beat of the segment is greater than or equal to 100, a distance from a starting point of the segment to the first heart beat is 0.3 seconds. When the heart rate of the first heart beat of the segment is less than or equal to 45, the distance from the starting point of the segment to the first heart beat is 0.37 seconds.

For ECG events with multiple segments, it is necessary to perform quality evaluation on the multiple segments, and calculate a proportion of non-interference signals of intercepted segments according to the signal quality evaluation index. When the proportion of the non-interference signals reaches a set threshold (preferably, the threshold is determined in a range of 60%-95%), the segments meet screening conditions, from which an optimal typical data segment is obtained.

Finally, the report table item data, the report graphic data and the report conclusion data are output.

In the present disclosure, in addition to the above process, manual check may also be performed based on obtained classification results, and the checked heart beat classification data, which is not in conformity with classification results output by automatic analysis is corrected, and fed back and input into to the trained model as training samples for artificial intelligence self-learning. The deep learning model may continuously carry out iterative loop training by inputting new training data, thereby continuously improving the accuracy of three classification models (interference two-classification model, heart beat classification model, ST segment and T wave change model) used by the present disclosure.

It should be noted that, although specific implementation manners of the three classification models are specifically described in the above-mentioned steps, it is not limited that the specific implementation may only be realized by the illustrated manners. All three models may be implemented by one or more of LeNet-5 model, AlexNet model, VGG16 model and Inception model, and other models such as ResNet model, RNN-related model, Auto-Encoding model or SeqToSeq model may also be used for training and classification inferring, and the number of categories classified by the models, and recognized ECG event types and heart rate parameters for statistical analysis are not limited.

Figure 7:
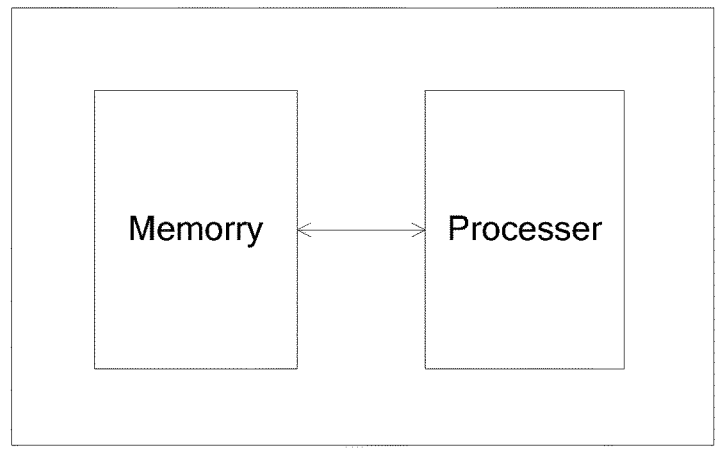
FIG. 7 is a schematic structure diagram illustrating an artificial intelligence self-learning-based ambulatory electrocardiogram analysis apparatus according to an embodiment of the present disclosure.

FIG. 7 is a schematic structure diagram illustrating an apparatus according to an embodiment of the present disclosure. The apparatus includes a processor and a memory. The memory may be connected to the processor via a bus. The memory may be a non-volatile memory, such as a hard disk drive and a flash memory, in which software programs and device drivers are stored. The software programs may perform various functions of the above method provided by the embodiment of the present disclosure. The device drivers may be a network and interface drivers. The processor is used for executing the software programs, and when the software programs are executed, the method provided by the embodiments of the present disclosure may be realized.

It should be noted that an embodiment of the present disclosure also provides a computer-readable storage medium. The computer-readable storage medium stores computer programs, and when the computer programs are executed by the processor, the method provided by the embodiments of the present disclosure may be realized.

An embodiment of the present disclosure also provides a computer program product including instructions. When the computer program product runs on a computer, the processor performs the above method.

In the artificial intelligence self-learning-based ambulatory ECG analysis method and apparatus according to the embodiments of the present disclosure, through data pre-processing, heart beat feature detection, interference signal detection by using a deep learning method, signal quality evaluation and lead combination, heart beat classification by using a deep learning method, heart beat verification, and analysis and calculation of ECG events and parameters, the report data is finally automatically output. The method is a complete and fast process automatic analysis method. The automatic analysis method of the present disclosure may also record modification information of automatic analysis results and collect modified data to feed back to the deep learning model for continuous training, thus continuously improving and enhancing the accuracy rate of the automatic analysis method.

Those skilled in the art should further realize that the units and algorithm steps of the examples described in the embodiments disclosed herein may be implemented in electronic hardware, computer software, or a combination of the two. In order to clearly illustrate the interchangeability of hardware and software, the composition and steps of each example have been generally described according to functions in the above description. Whether these functions are implemented in hardware or software depends on the specific application and design constraints of the technical solutions. Those skilled in the art may use different methods to implement the described functions for each specific application, but such implementation should not be considered to be beyond the scope of the present disclosure.

The steps of methods or algorithm described in the embodiments disclosed herein may be implemented in hardware, a software module executed by a processor, or a combination of the two. The software module may be placed in random access memory (RAM), memory, read only memory (ROM), electrically programmable ROM, electrically erasable programmable ROM, registers, hard disks, removable disks, CD-ROM, or any other form of storage medium known in the technical field.

The specific embodiments described above have further explained the purpose, technical solution and beneficial effects of the present disclosure in detail. It should be understood that the above is only specific embodiments of the present disclosure and is not used to limit the scope of protection of the present disclosure. Any modification, equivalent substitution, improvement, etc., made within the spirit and principles of the present disclosure should be included in the scope of protection of the present disclosure.

What is claimed is:
1. An artificial intelligence self-learning-based ambulatory electrocardiogram (ECG) analysis method, comprising:
receiving ambulatory electrocardiogram data output by an ambulatory electrocardiogram monitoring device; and converting a data format of the ambulatory ECG data into a preset standard data format by resampling, and performing a first filtering processing on converted ambulatory ECG data in the preset standard data format;

performing heart beat detection processing on ambulatory ECG data processed by the first filtering processing to identify multiple pieces of heart beat data comprised in the ambulatory ECG data, wherein each piece of heart beat data corresponds to a heart beat cycle, comprising amplitude and starting-ending time data of corresponding P wave, QRS complex and T wave;

determining a detection confidence level of each heart beat according to the heart beat data;

performing interference identification on the heart beat data according to a trained interference identification two-classification model to obtain whether there is interference noise in the heart beat data with a probability value for judging the interference noise;

determining a validity of the heart beat data according to the detection confidence level, and, according to lead parameters of determined valid heart beat data and the determined valid heart beat data, combining and generating heart beat time sequence data based on results of the interference identification and time rules; and generating heart beat analysis data according to the heart beat time sequence data;

performing feature extraction and analysis of an amplitude and time characterization data on the heart beat analysis data according to a trained heart beat classification model, to obtain primary classification information of the heart beat analysis data;

inputting the heart beat analysis data of particular heart beats in results of the primary classification information into a trained ST segment and T wave change model for identification, and determining ST segment and T wave evaluation information;

performing P wave and T wave feature detection on the heart beat analysis data according to the heart beat time sequence data to determine detailed feature information of P wave and T wave in each heart beat, wherein the detailed feature information comprises data of amplitudes, directions, forms and starting-ending time;

performing secondary classification processing on the heart beat analysis data according to ECG basic rule reference data, the detailed feature information of the P wave and the T wave and the ST segment and T wave evaluation information, under the primary classification information to finally obtain heart beat classification information;

analyzing and evaluating a signal quality of the heart beat analysis data, and obtaining a signal quality evaluation index of the heart beat analysis data;

analyzing and matching the heart beat classification information according to the ECG basic rule reference data, and processing a result of the analyzing and matching according to the signal quality evaluation index to generate ECG event data; and statistically analyzing the ECG event data to obtain corresponding report conclusion data and report table item data; evaluating the ECG event data according to the signal quality evaluation index to generate report graphic data; and outputting the report table item data, the report graphic data and the report conclusion data.

2. The artificial intelligence self-learning-based ambulatory electrocardiogram analysis method according to claim 1, wherein the determining a detection confidence level comprises:

determining an RR interval according to the heart beat data and calculating an estimation value of noise in the RR interval; and determining the detection confidence level of each piece of heart beat data according to the estimation value of the noise and a maximum amplitude in each piece of heart beat data.

3. The artificial intelligence self-learning-based ambulatory electrocardiogram analysis method according to claim 2, wherein the performing interference identification on the heart beat data according to a trained interference identification two-classification model comprises:

performing cutting and sampling on the heart beat data with a first data amount, and inputting data obtained by the cutting and sampling into the trained interference identification two-classification model to identify interference;

identifying a data segment with a heart beat interval greater than or equal to a preset interval determination threshold in the heart beat data;

performing a judgment of signal abnormality on the data segment with the heart beat interval greater than or equal to the preset interval determination threshold to determine whether the data segment is an abnormal signal;

if the data segment is not an abnormal signal, according to a set time value, determining a starting data point and an ending data point of sliding sampling in the data segment with a preset time width, and performing the sliding sampling on the data segment from the starting data point until the ending data point to obtain multiple sample data segments; and performing the interference identification on each of the multiple sample data segments.

4. The artificial intelligence self-learning-based ambulatory electrocardiogram analysis method according to claim 3, wherein the generating heart beat analysis data according to the heart beat time sequence data comprises:

cutting the heart beat data of each lead in the heart beat time sequence data according to a preset threshold to generate the heart beat analysis data of each lead.

5. The artificial intelligence self-learning-based ambulatory electrocardiogram analysis method according to claim 4, wherein the performing feature extraction and analysis of an amplitude and time characterization data on the heart beat analysis data according to a trained heart beat classification model, to obtain primary classification information of the heart beat analysis data comprises:

for the heart beat analysis data of a single lead, inputting the heart beat analysis data into the trained heart beat classification model corresponding to the single lead, performing the feature extraction and analysis of the amplitude and time characterization data with a second data amount, to obtain the primary classification information of the single lead.

6. The artificial intelligence self-learning-based ambulatory electrocardiogram analysis method according to claim 5, wherein the performing feature extraction and analysis of an amplitude and time characterization data on the heart beat analysis data according to a trained heart beat classification model, to obtain primary classification information of the heart beat analysis data comprises:

according to the trained heart beat classification model corresponding to each lead, performing the feature extraction and analysis of the amplitude and time characterization data on the heart beat analysis data of each lead with a third data amount, to obtain classification information of each lead; and performing classification voting decision calculation according to the classification information of each lead and lead weight reference coefficients, to obtain the primary classification information.

7. The artificial intelligence self-learning-based ambulatory electrocardiogram analysis method according to claim 1, wherein the performing interference identification on the heart beat data according to a trained interference identification two-classification model comprises:

performing cutting and sampling on the heart beat data with a first data amount, and inputting data obtained by the cutting and sampling into the trained interference identification two-classification model to identify interference;

identifying a data segment with a heart beat interval greater than or equal to a preset interval determination threshold in the heart beat data;

performing a judgment of signal abnormality on the data segment with the heart beat interval greater than or equal to the preset interval determination threshold to determine whether the data segment is an abnormal signal;

if the data segment is not an abnormal signal, according to a set time value, determining a starting data point and an ending data point of sliding sampling in the data segment with a preset time width, and performing the sliding sampling on the data segment from the starting data point until the ending data point to obtain multiple sample data segments; and performing the interference identification on each of the multiple sample data segments.

8. The artificial intelligence self-learning-based ambulatory electrocardiogram analysis method according to claim 1, wherein the generating heart beat analysis data according to the heart beat time sequence data comprises:

cutting the heart beat data of each lead in the heart beat time sequence data according to a preset threshold to generate the heart beat analysis data of each lead.

9. The artificial intelligence self-learning-based ambulatory electrocardiogram analysis method according to claim 1, wherein the performing feature extraction and analysis of an amplitude and time characterization data on the heart beat analysis data according to a trained heart beat classification model, to obtain primary classification information of the heart beat analysis data comprises:

for the heart beat analysis data of a single lead, inputting the heart beat analysis data into the trained heart beat classification model corresponding to the single lead, performing the feature extraction and analysis of the amplitude and time characterization data with a second data amount, to obtain the primary classification information of the single lead.

10. The artificial intelligence self-learning-based ambulatory electrocardiogram analysis method according to claim 1, wherein the performing feature extraction and analysis of an amplitude and time characterization data on the heart beat analysis data according to a trained heart beat classification model, to obtain primary classification information of the heart beat analysis data comprises:

according to the trained heart beat classification model corresponding to each lead, performing the feature extraction and analysis of the amplitude and time characterization data on the heart beat analysis data of each lead with a third data amount, to obtain classification information of each lead; and performing classification voting decision calculation according to the classification information of each lead and lead weight reference coefficients, to obtain the primary classification information.

11. The artificial intelligence self-learning-based ambulatory electrocardiogram analysis method according to claim 1, wherein the performing feature extraction and analysis of an amplitude and time characterization data on the heart beat analysis data according to a trained heart beat classification model, to obtain primary classification information of the heart beat analysis data comprises:

according to a trained multi-lead synchronous correlation classification model, performing the feature extraction and analysis of a synchronous amplitude and the time characterization data on the heart beat analysis data of each lead with a fourth data amount, to obtain the primary classification information of the heart beat analysis data.

12. The artificial intelligence self-learning-based ambulatory electrocardiogram analysis method according to claim 1, wherein the analyzing and evaluating a signal quality of the heart beat analysis data, and obtaining signal quality evaluation index of the heart beat analysis data comprises:

extracting signals of RR intervals in the heart beat analysis data, performing second filtering processing and envelope calculation on the signals of the RR intervals to determine a noise signal intensity, and calculating a signal-to-noise ratio of a maximum amplitude of corresponding heart beat time sequence data to determine the signal quality evaluation index.

13. The artificial intelligence self-learning-based ambulatory electrocardiogram analysis method according to claim 1, wherein the inputting the heart beat analysis data of particular heart beats in results of the primary classification information into a trained ST segment and T wave change model for identification, and determining ST segment and T wave evaluation information comprises:

inputting data of the particular heart beats in the primary classification into the trained ST segment and T wave change model according to leads in turn, performing the feature extraction and analysis of the amplitude and time characterization data on the data of the particular heart beats of each lead to obtain ST segment and T wave change information of each lead, and determining the ST segment and T wave evaluation information, which is lead position information that indicates the ST segment and T wave corresponding to heart beat segment data occur change.

14. The artificial intelligence self-learning-based ambulatory electrocardiogram analysis method according to claim 1, wherein the performing P wave and T wave feature detection on the heart beat analysis data to determine detailed feature information comprises:

performing QRS complex signal elimination processing on the heart beat analysis data, and performing third filtering on heart beat analysis data after the QRS complex signal elimination processing, performing data separation on the heart beat analysis data by an independent component analysis algorithm to obtain sequence data of each independent component, according to distribution characteristics of peak values of the sequence data of the independent component and a position of the QRS complex, selecting an independent component with the highest probability as corresponding P wave and T wave components, and determining direction and morphology features of the P wave and the T wave.

15. The artificial intelligence self-learning-based ambulatory electrocardiogram analysis method according to claim 1, wherein the performing P wave and T wave feature detection on the heart beat analysis data to determine detailed feature information comprises:
performing P wave and T wave signal feature extraction processing on the heart beat analysis data;
performing peak detection on signal feature data, determining a T wave detection interval between two adjacent QRS complexes, and determining a data point with a maximum amplitude in the T wave detection interval as the T wave;
determining a data point with a maximum amplitude in an interval other than the T wave detection interval between the two adjacent QRS complexes as the P wave; and
determining direction and morphology features of the P wave and the T wave according to peak values and position data of the P wave and the T wave.

16. The artificial intelligence self-learning-based ambulatory electrocardiogram analysis method according to claim 1, wherein the evaluating the ECG event data according to the signal quality evaluation index to generate report graphic data comprises:
performing evaluation on data segments of each type of ECG event according to the signal quality evaluation index, and selecting the data segments with the highest signal quality evaluation index as typical data segments in the ECG event to generate the report graphic data.

17. The artificial intelligence self-learning-based ambulatory electrocardiogram analysis method according to claim 1, wherein the method further comprises:
receiving modification information of the heart beat classification information; and
taking modified data as training sample data for model training in the artificial intelligence self-learning-based electrocardiogram automatic analysis method.

18. A computer program product comprising instructions, wherein when the computer program product runs on a computer, the computer executes the method of claim 1.

19. A computer-readable storage medium, comprising instructions, wherein when the instructions run on a computer, the computer executes the method of claim 1.

* * * * *

UNITED STATES PATENT AND TRADEMARK OFFICE
CERTIFICATE OF CORRECTION

PATENT NO. : 11,234,629 B2  
APPLICATION NO. : 16/651912  
DATED : February 1, 2022  
INVENTOR(S) : Chang Liu et al.

Page 1 of 1

It is certified that error appears in the above-identified patent and that said Letters Patent is hereby corrected as shown below:

In the Claims

| | | | |
|---|---|---|---|
| Claim 12, | Column 28, | Line 23, | change "Theartificial" to --The artificial-- |
| Claim 12, | Column 28, | Line 30, | change "on the signals" to --on the extracted signals-- |
| Claim 17, | Column 30, | Line 16, | change "electrocardiogram automatic analysis" to --ambulatory electrocardiogram analysis-- |

Signed and Sealed this  
Eighth Day of March, 2022

Drew Hirshfeld  
*Performing the Functions and Duties of the*  
*Under Secretary of Commerce for Intellectual Property and*  
*Director of the United States Patent and Trademark Office*